United States Patent [19]

Grinda et al.

[11] Patent Number: 4,698,222

[45] Date of Patent: Oct. 6, 1987

[54] EXTRACTION OF INSECTICIDES FROM PLANTS

[75] Inventors: Françoise Grinda, Vallauris; Jean Gueyne, Paris, both of France

[73] Assignee: SAPHYR S.A.R.L., France

[21] Appl. No.: 576,385

[22] PCT Filed: Apr. 28, 1983

[86] PCT No.: PCT/FR83/00079

§ 371 Date: Jan. 13, 1984

§ 102(e) Date: Jan. 13, 1984

[87] PCT Pub. No.: WO83/03951

PCT Pub. Date: Nov. 24, 1983

[30] Foreign Application Priority Data

May 14, 1982 [FR] France .............................. 82 08436

[51] Int. Cl.$^4$ ............................................ A01N 65/00
[52] U.S. Cl. ........................................ 421/195; 514/68; 424/DIG. 8

[58] Field of Search .............. 424/195, 279, 283, 285, 424/189, 186, 289, 312, DIG. 8; 514/68

[56] References Cited

U.S. PATENT DOCUMENTS

| | | | |
|---|---|---|---|
| 2,149,917 | 4/1936 | Kilgore | 424/189 |
| 2,267,385 | 12/1941 | Whitmino | 424/DIG. 9 |
| 2,374,918 | 5/1945 | Brown | 514/68 |
| 2,428,494 | 10/1947 | Jones et al. | 514/68 |

FOREIGN PATENT DOCUMENTS

| | | | |
|---|---|---|---|
| 2448856 | 9/1980 | France | 424/195 |
| 552879 | 4/1943 | United Kingdom | 514/68 |

*Primary Examiner*—Johnnie R. Brown
*Assistant Examiner*—John W. Rollins
*Attorney, Agent, or Firm*—Ostrolenk, Faber, Gerb & Soffen

[57] ABSTRACT

Extraction of insecticide from plants by means of an organic solvent boiling at a temperature exceeding 100° C. The solvent is formed of an aliphatic acid ester from $C_6$ to $C_{30}$ and preferably from $C_8$ to $C_{20}$.

17 Claims, No Drawings

EXTRACTION OF INSECTICIDES FROM PLANTS

The present invention refers to an improvement in the extraction of insecticidal substances from plants by means of organic solvents.

The treatment by different organic solvents of plants which contain insecticidal substances has been the object of extensive work in the past; the only solvents which have given industrial results are chlorinated hydrocarbons, in particular methylene chloride and chloroform, which dissolve large quantities of insecticidal substances. Thus, one of the most important products, rotenone, is readily extracted, Cparticularly from derris, by means of said solvents, in which it is soluble in an amount of 58.2 g and 73.4 g respectively in 100 ml of solvent. However, it is not stable in such solutions and it is practically impossible to obtain it in pure form. Furthermore, while it is possible to effect an extraction with chlorinated solvents in a factory where all necessary health precautions are taken, the insecticide cannot be used in solution, in these unhealthy solvents, for the spraying of surfaces or objects infested by insects. The goal of extracting insecticides by means of an absolutely harmless solvent which makes it possible to obtain the insecticide in the desired state of purity is therefore still present.

The present invention fills this gap in the prior art. It makes it possible to extract the insecticidal materials contained in the plants by means of liquids which are entirely harmless, both to man and to animals. This new process also makes it possible to obtain the insecticide, and particularly rotenone, in highly concentrated state.

The invention is based on the unexpected finding that esters of aliphatic acids of sufficiently high molecular weight make it possible to dissolve the insecticidal substance, in particular rotenone.

This finding is all the more surprising since it has been known for a long time that fats, particularly cottonseed or olive oils, or otherwise stated glycerin esters of different fatty acids, are poor solvents for rotenone. It is therefore surprising to find that alkyl esters, for instance, the butyl, hexyl, and octyl esters, etc. of fatty acids such as lauric, oleic, or stearic acid, dissolve rotenone.

The process of the invention, which involves treating a dry plant containing an insecticide principle with an organic solvent so as to extract the insecticide and separating the resultant solution from the residues of the plant, is characterized by the fact that the solvent employed is an aliphatic ester containing at least 12 carbon atoms, preferably 18 to 36 carbon atoms.

The preferred solvents in accordance with the invention are alkyl or alkenyl esters having 1 to 16 carbon atoms of $C_6$ to $C_{30}$, or better $C_8$ to $C_{20}$, aliphatic acids.

Thus one can employ to advantage methyl, ethyl, propyl, isopropyl, butyl, amyl, hexyl, octyl, isooctyl, nonyl, lauryl and oleyl caprylates, caprates (decanoates), undecanoates, laurates, myristates, palmitates, oleates, ricinoleates, linoleates, linolenates, stearates, arachidates, lignoceates, cerotates, cetoleates, erucitates, etc., or the like.

The process of the invention can be carried out in different ways. One may use the above-defined ester to treat the dry power of the plant containing the insecticidal substance. However, as the esters in question are more or less viscous while the powdered mass to be treated is rather voluminous as compared with the amount of solvent used, the operation becomes easier if the extraction medium is diluted with a lighter solvent, in particular a chlorinated hydrocarbon.

Another, more advantageous method consists in effecting a first extraction in the conventional manner, using chlorinated solvents so as to obtain an enriched extract or what is ordinarily called a "resin", which may contain, for instance, about 40% rotenone, and then subjecting the latter to extraction with the esters according to the invention. In this way, one can obtain highly concentrated products, namely containing more than 90% rotenone or other insecticides.

The solvents of the present invention may also be used as adjuvants to known solvents, whose action they improve. Thus, in accordance with a variant of the invention, the extraction of an insecticide from a plant can be effected by means of a mixture of dialkyl phthalate with one or more of the aliphatic acid esters defined above. One may, for instance, use mixtures of 10 to 70% of a phthalate with 90 to 30% of ester respectively.

Ternary mixtures of solvents, comprising esters in accordance with the present invention, with phthalates and chlorinated solvents known per se, lead to high extraction yields, while the final elimination of the chlorinated compound is facilitated.

When it is not desired to prepare a powder of pure rotenone, tephrosin, deguelin, toxicarol, pyrethrum or the like but only a solution which can be used directly, the solutions of the invention are entirely suitable since the esters, particularly those of fatty acids, are entirely harmless and have a very high vapor tension. Furthermore these solutions, which can be dosed in different concentrations of for instance between 5 and 40%, may also be emulsified with water, the emulsion being used for the desired application.

The process of the invention is applicable to the different plants containing insecticides, particularly resins, leaves or seeds of species such as

*Lonchocarpus Nicou* (known as cube or barbasco)
*Lonchocarpus Urucu*
*Milletia ferruginea* (French West Africa)
*Milletia pachycarpa* (Malaysia)
*Mundulea suberosa* (Africa)
*Pachyrhyzus tuberosus*
*Pachyrhyzus tephrosia*
*Piscidia erythrina*
*Herba Piret:* Derris powder, for example from *Derris elliptica* can also be used.

The invention is illustrated, but not limited, by the following examples.

EXAMPLE 1

100 g of finely crushed derris powder are introduced into a 250 ml round-bottom flask provided with agitator; 25 g of octyl stearate are added and 160 g of methylene chloride are then slowly poured into the mixture.

After agitating for half an hour at 45° C., the treated powder is separated from the liquid by filtration and washed on the filter with 50 g of methylene chloride. The liquid obtained, including the wash liquid, is introduced into a round-bottom flask with reflux condenser, in which the methylene chloride is distilled so as to recover it.

There are obtained 39 g of a viscous liquid containing 36% extracted rotenone substances and 64% octyl stearate. The rotenone content of this product is 14%. By diluting this product with an equal volume of octyl stearate a 7% rotenone solution is obtained which can be used directly as an insecticide composition.

A fraction of the viscous product is emulsified, in the presence of a surface active agent with 10 times its volume of water, to serve as spray for plants in order to protect them against insects.

EXAMPLE 2

The operations of Example 1 are repeated, using butyl stearate instead of octyl stearate. The same results are obtained.

EXAMPLE 3

With a preparation similar to that of Example 1, 25 g of hexyl laurate are used instead of octyl stearate.

The 38 g of product obtained contain 13.6% rotenone.

EXAMPLE 4

Proceeding in the same manner as in Example 1, lauryl caprate is used instead of octyl stearate. Similar results are obtained.

EXAMPLE 5

1 kg of commercial rotenone extract, containing 40% rotenone, known under the name of "resin", is dissolved in 1 kg of hot butyl laurate.

To the resultant solution there is added 10% sodium lauryl sulfonate as emulsifier, which makes it possible, by dilution with water, to obtain a stable emulsion containing 4% rotenone, suitable for the direct treatment of plants by spraying.

EXAMPLE 6

To 200 g of derris, reduced to a fine powder, there are added 25 g of octyl stearate and 350 g of chloroform; the mixture is agitated for 15 minutes at ordinary temperature. After filtration of the mixture, the residue is washed on the filter with 75 g of chloroform.

The chloroform is expelled by distillation at 74° C. from the resultant filtrate in order to recover it. The remaining solution in the octyl stearate is treated with 60 g of methyl alcohol, with agitation. This results in a precipitation of rotenone crystals, which are removed by filtration and washed with a new portion of 50 g of alcohol.

After drying the crystals which have thus been obtained, it is noted that this product consists of rotenone which is stable in air and light, contrary to the product of the prior art, which was unstable.

EXAMPLE 7

The operations of Example 6 are repeated with propyl oleate instead of octyl stearate, and once again stable rotenone is obtained.

EXAMPLE 8

1 kg of powdered *Herba piretri* is crushed with 1 liter of isoamyl caprylate and heated at 70° C. for one hour. The mixture is then diluted with 1 liter of ethylene glycol acetate and the liquid is removed from the powder by centrifuging.

The liquid which has been removed is emulsified in 6 liters of water in the presence of a nonyl-phenyl-polyoxyethylene as surface active agent. The emulsion constitutes an excellent insecticide which can be sprayed without any danger for warm-blooded animals.

EXAMPLE 9

The manner of procedure of Example 1 is repeated with, in addition, 15 g of dimethyl orthophthalate, the amount of methylene chloride being reduced to 145 g.

The sequence of the operations is the same as in Example 1; a 7.8% solution of rotenones is obtained.

EXAMPLE 10

In the formulation of Example 6, the 25 g of octyl stearate are accompanied by 20 g of diethyl phthalate. The extraction is faster.

EXAMPLE 11

1 kg of commercial rotenone extract containing 40% rotenone is dissolved in a solvent mixture consisting of
300 g of methyl oleate
300 g of di-isopropyl orthophthalate
400 g of 1,2-dichlorethane.

The dichlorethane is then eliminated by distillation and the liquid obtained contains 66% rotenone.

EXAMPLE 12

An insecticide extract is prepared by the method of Example 6 from 200 g of finely powdered roots and leaves of *Lonchocarpus Urucu*.

What is claimed is:

1. A method of extracting a natural insecticidal substance from a plant containing the insecticidal substance selected from the group consisting of *Lonchocarpus Nicou, Lonchocarpus Urucu, Milletia ferruginea, Milletia pachycarpa, Mundulea suberosa, Pachyrhyzus tuberosus, Pachyrhyzus tephrosia, Piscidia erythrina, Herba pireta* and derris which comprises contacting powdered dry parts of the plant with an alkyl or alkenyl ester of a fatty acid, in which the ester moiety contains 1 to 16 carbon atoms and the fatty acid moiety contains 6 to 30 carbon atoms, and thereafter recovering the ester having the natural insecticide substance dissolved therein.

2. The method of claim 1 in which said ester moiety contains 1 to 12 carbon atoms and the fatty acid moiety contains 6 to 18 carbon atoms.

3. The method of claim 2 in which the ester is methyl, ethyl, propyl, isopropyl, butyl, hexyl, octyl or lauryl caprylate, caprate, laurate, stearate or oleate.

4. The method of claim 3 in which the ester moiety is oleyl.

5. The method of claim 1 in which a chlorinated hydrocarbon extractant having one to two carbon atoms is employed in combination with said ester, the combined chlorinated hydrocarbon and ester are recovered and the ester is separated from the chlorinated hydrocarbon.

6. The method of claim 5 in which the chlorinated hydrocarbon is methylene chloride, chloroform or dichloroethane.

7. The method of claim 6 in which the weight of the chlorinated hydrocarbon is 0.4–1.75 per unit weight of the powdered plant or extract and the weight of the ester is 12.5–30% of the weight of the powdered plant or extract.

8. The method of claim 5 in which a dialkyl phthalate is employed in combination with said ester in a ratio of 10–70 parts by weight of phthalate, and 90–30 parts by weight of ester, the alkyl groups of the phthalate having 1 to 3 carbon atoms.

9. The method of claim 1 in which a dialkyl phthalate is employed in combination with said ester in a ratio of 10–70 parts by weight of phthalate, and 90–30 parts by weight of ester, the alkyl groups of the phthalate having 1 to 3 carbon atoms.

10. A method of extracting rotenone from a plant material which comprises contacting a derris plant material containing rotenone with an alkyl or alkenyl ester of a fatty acid, in which the alkyl or alkenyl moiety has 1 to 16 carbon atoms and the fatty acid moiety has 6 to 30 carbon atoms, for a time sufficient for rotenone to dissolve in the ester, and then separating the ester from said plant material.

11. The method of claim 10, in which the alkyl or alkenyl moiety has 1 to 12 carbon atoms and the fatty acid moiety has 6 to 18 carbon atoms.

12. An insecticidal composition comprising a solution comprising an alkyl or alkenyl ester of a fatty acid in which the ester moiety has 1 to 16 carbon atoms and the acid moiety has 6 to 30 carbon atoms containing dissolved therein 4 to 90% by weight of natural insecticidal substance of a plant containing the insecticidal substance selected from the group consisting of *Longchocarpus Nicou, Lonchocarpus Urucu, Milletia ferruginea, Milletia pachycarpa, Mundulea suberosa, Pachyrhyzus tuberosus, Pachyrhyzus tephrosia, Piscidia erythrina, Herba pireta* and derris.

13. The insecticidal composition of claim 12 which the amount of natural insecticidal substance is 7 to 66%.

14. The insecticidal composition of claim 13 in which the amount of natural insecticidal substance is 5 to 40%, the ester moiety has 1 to 12 carbon atoms and the fatty acid moiety has 6 to 18 carbon atoms.

15. The insecticidal composition of claim 12 containing 10 to 70 parts by weight of a dialkyl phthalate whose alkyl groups having 1 to 3 carbon atoms, per 90 to 30 parts by weight of said ester.

16. The insecticidal composition of claim 15 in which said natural insecticidal substance is rotenone.

17. An insecticidal composition comprising a solution of 5 to 40% by weight of rotenone in a fatty acid alkyl or alkenyl ester, in which the alkyl or alkenyl moiety has 1 to 12 carbon atoms and the fatty acid moiety has 6 to 18 carbon atoms.

* * * * *